(12) United States Patent
Jekkel et al.

(10) Patent No.: US 6,905,851 B1
(45) Date of Patent: Jun. 14, 2005

(54) **HYDROXYLATION OF COMPACTIN PRAVASTATIN BY *MICROMONOSPORA***

(75) Inventors: Antónia Jekkel, Budapest (HU); Gábor Ambrus, Budapest (HU); Éva Ilkóy, Budapest (HU); Ildikó Horváth, Budapest (HU); Attila Kónya, Dunakeszi (HU); István Mihály Szabó, Budapest (HU); Zsuzsanna Nagy, Budapest (HU); Gyula Horváth, Budapest (HU); Júlia Mózes, Ecser (HU); István Barta, Budapest (HU); György Somogyi, Budapest (HU); János Salát, Budapest (HU); Sándor Boros, Szöd (HU)

(73) Assignee: IVAX Drug Research Institute, Budapest (HU)

( * ) Notice: Subject to any disclaimer, the term of this patent is extended or adjusted under 35 U.S.C. 154(b) by 348 days.

(21) Appl. No.: 10/030,726

(22) PCT Filed: Jun. 29, 2000

(86) PCT No.: PCT/HU00/00066

§ 371 (c)(1),
(2), (4) Date: Jun. 4, 2002

(87) PCT Pub. No.: WO01/04340

PCT Pub. Date: Jan. 18, 2001

(30) Foreign Application Priority Data

Jul. 12, 1999 (HU) ............................................. 9902352

(51) Int. Cl.$^7$ .......................... C12P 17/06; C12P 17/42
(52) U.S. Cl. ..................... 435/135; 435/146; 435/252.1
(58) Field of Search ................................. 435/135, 146

(56) References Cited

U.S. PATENT DOCUMENTS

| | | |
|---|---|---|
| 4,346,227 A | 8/1982 | Terahara et al. |
| 4,448,979 A | 5/1984 | Terahara et al. |
| 4,537,859 A | 8/1985 | Terahara et al. |
| 5,179,013 A | 1/1993 | Matsuoka et al. |

FOREIGN PATENT DOCUMENTS

| | | |
|---|---|---|
| JP | 58010572 | 1/1983 |
| WO | WO 96/40863 | 12/1996 |

OTHER PUBLICATIONS

Endo et al., *J. Antibiotics* 29:1346–1348 (1976).
Endo et al., *FEBS Let.* 72:323–326 (1976).
Kuo et al. *J. Org. Chem.* 48:1991–1998 (1983).
Arai et al. *Sankyo Kenkysuho Nemp.* 40:1–38 (1988).
Serizawa et al. *J. Antibiotics* 36:887–891 (1983).
Matsuoka et al. *Eur. J. Biochem.* 184:707–713 (1989).
Bergey's Manual of Syst. Bact., p. 2448 (1989).
Kawamoto et al. *Agric. Biol. Chem.* 47:203–215 (1983).

*Primary Examiner*—Herbert J. Lilling
(74) *Attorney, Agent, or Firm*—Michael A. Steinberg

(57) ABSTRACT

The present invention relates to a new microbial process for the preparation of compound of formula (I) from a compound of general formula (II) wherein R stands for an alkali metal or ammonium ion, by the submerged culture of a strain which is able to 6β-hydroxylate the compound of formula (II) in aerobic fermentation and by the separation and purification of the product of formula (I) formed in the course of the bioconversion. The latter comprises the cultivation of a *Micromonospora* strain which is able to 6β-hydroxylate a compound of general formula (II)—wherein R is as defined above—at 25–32° C. on a nutrient medium containing available carbon—and nitrogen sources and mineral salts, thereafter feeding the substrate to be transformed into the developing culture, then hydroxilating the substrate until finishing of the bioconversion, then separating the compound of formula (I) from the culture broth and, if desired, purifying the same.

7 Claims, No Drawings

HYDROXYLATION OF COMPACTIN PRAVASTATIN BY *MICROMONOSPORA*

The present invention relates to a new microbial process for the preparation of pravastatin.

More particularly, this invention relates to a microbial process for the preparation of pravastatin of formula (I)

(I)

from a compound of the general formula (II)

(II)

wherein R stands for an alkali metal or ammonium ion, with a microorganism, wherein said microorganism is a prokaryote from genus *Micromonospora*, which is able to hydroxylate a compound of the general formula (II) at the 6β-position.

The hypercholesterolaemia has been recognized as a major risk factor for atherosclerotic disease, specifically for coronary heart disease. During the past two decades 3-hydroxy-3-methylglutaryl-coenzyme A reductase (HMG-CoA reductase EC, 1.1.1.34) as the major rate-limiting enzyme in the cholesterol biosynthesis, has been extensively studied. Mevinolln and related compounds biosynthesised by selected strains of different fungal species were found to be competitive inhibitors of this enzyme [Endo, A. et al., J. Antibiotics 29, 1346–1348 (1976); Endo, A. et al., FEBS Lett. 72, 323–326 (1976); Kuo, C. H. et al., J. Org. Chem. 48, 1991–1998 (1983)].

Pravastatin is also a member of the family of HMG-CoA reductase inhibitors. At first, pravastatin was found as a minor urinary metabolite of compactin in dog (Tanaka, M. et al., unpublished) in the course of metabolic studies of compactin [Arai, M. et al. Sankyo Kenkyusho Nempo, 40, 1–38 (1988)].

The main characteristic property of pravastatin as the hydroxylated product of compactin is its tissue selectivity. This drug strongly inhibits sterol synthesis in liver and in intestine, but weakly in other organs. It is advantageous that pravastatin possesses lower toxicity than the other HMG-CoA reductase inhibitors.

It has been reported that microbial hydroxylation of compactin can be accomplished in various extent by several strains of species belonging to many different genera of fungi, and by strains of actinomycete species belonging to the genera *Nocardia, Actinomadura* and *Streptomyces,* among others *Streptomyces roseochromogenes* and *Streptomyces carbophilus* (U.S. Pat. No. 5,179,013, U.S. Pat. No. 4,448,979, U.S. Pat. No. 4,346,227, U.S. Pat. No. 4,537,859, Japanese Patent No. 58,010,572).

A problem with using fungi for the production of pravastatin from compactin is that these organisms generally do not tolerate higher concentrations of compactin in liquid culture media, presumably due to is antifungal activity [Serizawa, N. et al., J. Antibiotics 36, 887–891 (1983)]. In *Streptomyces carbophilus* the cytochrome P450 system has been shown to be required for the hydroxylation of compactin to pravastatin [Matsuoka, T. et al., Eur. J. Biochem. 184, 707–713 (1989)]. Difficulty of genetic improvement of the ability of hydroxylation with the use of such an enzyme is that it is a complex of proteins rather than a single protein.

Our investigation were focused on finding an actinomycete strain which would produce pravastatin from salts of acidic form of compactin with higher yield and by applying higher substrate concentration in the bioconversion than those known from former patent specifications.

During the screening, covering about 6000 actinomycetes, mostly our own isolates, but also authentic strains from international strain collections, five *Streptomyces* and five *Micromonospora* were selected for further studies, because they proved to be able to hydroxylate the sodium salt of the acidic form of compactin into pravastatin. These ten actinomycete strains, from which eight strains have been taxonomically identified at species level in our laboratory, were the following:

*Streptomyces violaceus* (according to Kampfer et al, 1991), strain No. 1/43,

*Streptomyces rochei* (Berger et al., 1949; Waksman and Lechevalier, 1953), strain No. 1/41.

*Streptomyces resistomycificus* (Lindenbein, 1952), strain No. 1/44.

*Streptomyces* sp., strain No. 1/28.

*Streptomyces lanatus,* (Frommer, 1959), strain No. 1/16.

*Micromonospora* sp., strain No. IDR-$P_3$.

*Micromonospora purpurea* (Luedemann and Brodsky, 1964), strain No. IDR-$P_4$.

*Micromonospora echinospora* (Luedemann and Brodsky, 1964), strain No. IDR-$P_5$.

*Micromonospora megalomicea* (Weinstein et al., 1969), strain No. IDR-$P_6$.

*Micromonospora rosaria* (Horan and Brodsky, 1986), strain No. IDR-$P_7$.

Since, up to now, there are no data in the literature on the ability of *Micromonospora* to convert salts of the acidic form of compactin into pravastatin, we have thoroughly studied not only this particular enzymatic ability, but also the taxonomic position of these above listed strains of *Micromonospora.*

Taxonomic Position of Strains IDR-$P_3$, -$P_4$, -$P_5$, -$P_6$ and -$P_7$ at Generic Level All of these strains produced well developed mycelia, composed of branched hyphae of about 0.4–0.7 μm in diameter. Aerial mycelium is absent or occurs only in traces. Nonmotile spores are borne on sporophores singly. Hyphae of the substrate mycelium are Gram-positive and not acid-fast. Strains Nos. IDR $P_3$–$P_7$ are aerobic, chemoorganotrophic and sensitive to pH below 6.0. Walls contain meso-diaminopimelic acid. The above listed diagnostic properties—as key characters—clearly demonstrate, that these monosporic actinomycete strains are typical members of the genus *Micromonospora.*

Taxonomic Description of *Micromonospora* sp., Strain No. IDR-P$_3$

Micromorphological properties: Substrate mycelium is composed of well developed, more curved than straight, monopodially branching filaments. Spores on the sporophores are single, spherical approximately 1.8 μm in diameter and dispersing more or less evenly on hyphal filaments. Spores are either sessile or on the end of short sporophores. In broth cultures spores were not observed on the hypae presumably because the release of mature spores is very quick.

Cultural-macromorphological Properties:

Czapek-sucrose agar: Medium growth, the colonies have reddish colour covered by point-like black sporulating areas.

Glucose-asparagine agar: The growth was recorded as point like and elevated, reddish-brown or black colonies. Reddish diffusible pigments.

Nutrient agar: Fair growth, elevated, reddish-brown or black colonies. Reddish-brown exopigment in the medium.

Yeast extract-malt extract agar (ISP Med. 2): Well developed, elevated and wrinkled, brown colonies, covered partly with black sporulating areas or with "pseudo-aerial mycelium" (this is appearing as a restricted whitish or greyish bloom). Brownish or brownish-red soluble pigment.

Inorganic salts-starch agar (ISP Med. 4): Medium growth of reddish-brown elevated and wrinkled colonies. Light reddish soluble pigment.

Glycerol-asparagine agar (ISP Med. 5): Growth only in traces, off-white or light orange coloured, flat colonies, light rose soluble pigment.

Carbon source utilization: Good growth on and positive utilization of L-arabinose, D-galactose, D-fructose, D-glucose, D-xylose, lactose, melibiose, sucrose, D-mannitol, dulcitol, glycerol and inositol. Growth with L-rhamnose, D-raffinose and inulin was slightly better than on the negative control medium. Nitrogen source utilization: Good growth with yeast extract and NZ-Amine, no or weak utilization of NaNO$_3$.

Other physiological-biochemical properties: Cellulose and starch are hydrolyzed, milk is digested strongly. Nitrate reduction test is negative. No growth on potato slices without calcium carbonate (pH 5.8–6.0). No melanoid pigment production.

This strain No. IDR-P$_3$ of *Micromonospora* sp. was isolated from a mud sample of Lake Balaton (Hungary).

Systematic position: Further comparative systematic studies would be necessary to clarify the exact taxonomic position of this strain among the species of the genus *Micromonospora*. On the basis of certain properties it seems to be not impossible, that strain IDR-P$_3$ represents a new species within the genus *Micromonospora*.

Differential-diagnostic Description and Identification of *Micromonospora* Strains IDR-P$_4$, -P$_5$, -P$_6$ and P$_7$ Strain IDR-P$_4$ On the above listed diagnostic media, generally, good growth, orange to orange red, red, sometimes yellowish or rose coloured colonies. Soluble pigments and aerial mycelium are not produced. The number of solitary spores is relatively low. They occur on the sporophores terminally. Substrate mycelium is composed of well branching hypae. Aerial mycelium absent. No growth on D-melibiose, raffinose, mannitol, glycerol, lactose, L-rhamnose but good growth on D-arabinose, glucose, D-xylose and weak growth on D-galactose and D-fructose. On the basis of these conventional diagnostic properties we have identified this strain as a member of species *Micromonospora purpurea* (Luedemann and Brodsky, 1964).

Strain IDR-P$_5$

This strain produces mostly solitary sporophores and sphaerical dark brown to black spores (0.8–1.5 μm in diameter) which adhere firmly to the sporophores until maturation. According to our electromicroscopic observations, on the surface of these spores warty structures or outgrowths ("blunt spines" according to the Vol. 4 of Bergey's Manual of Syst. Bact. 1989, pages 2448) can be observed, which is very characteristic of the spores of *Micromonospora echinosora*. Otherwise, the cultural-morphological and physiological diagnostic properties of this strain are also very similar to those of the *M. echinospora*. The colour of the well developed colonies on the standard diagnostic media is orange-brown or dark purple. The sporulating layer is black or purplish black, waxy. Aerial mycelium absent. Melanin pigment not produced. Milk digested. Good growth on D-xylose, D-arabinose, D-glucose, and sucrose, but no growth with L-rhamnose, raffinose, D-galactose, D-fructose, D-melibiose and glycerol. We consider this strain as a typical member of *Micromonospora echinospora*.

Strain IDR-P$_6$

On the majority of diagnostic media moderate to weak growth. The orange or orange red colonies consist of long branched filaments (appr. 0.6 μm in diameter) and a limited number of solitary, sphaerical, dark coloured spores (0.6–1.0 μm in diameter). Does not produce aerial mycelium. In certain media weak reddish or rose coloured soluble pigments are formed. On tyrosine agar melanoid pigments were not produced. On a basal medium the following carbon sources have been utilized by this strain: D-xylose and D-fructose; only weakly; D-melibiose, mannitol and galactose, but no or sporadic growth was observed with glycerol, L-rhamnose, lactose and raffinose (see also Kawamoto, I. et al.: Agric. Biol. Chem., 47, 203–215, 1983). Strain No. IDR-P$_6$ shows a considerable similarity to the species *Micromonospora megalomicea*, (Weinstein, 1972) and we consider it as a member of this species.

Strain IDR-P$_7$

Good to moderate growth on Bennett agar, Czapek sucrose agar, glucose-asparagine agar, nutrient agar, oatmeal agar, potato-dextrose agar, etc. The colour of the vegetative mycelial pigments ranges from reddish-brown to purplish-brown. On certain media wine red diffusible pigments are formed. On the surface of the colonies black spots are frequently produced. Vegetative hyphae (average diameter: 0.5 μm) are intensively branched. Spores (1.4–1.7 μm in diameter) are borne singly, sessile or on short sporophores and occur along the length of the hypae. Growth and sporulation are of open web type or Luedemann. The following compounds are utilized by this strain as only source of carbon in medium: D-glucose, lactose, D-mannitol, L-rhamnose, sucrose and D-xylose. Dulcitol, glycerol, D-melibiose and D-raffinose are not utilized. We have identified strain No. IDR-P$_7$ as a typical member of *Micromonospora rosaria* (Horan and Brodsky, 1986).

The above presented *Micromonospora* strains were deposited at the National Collection of Agricultural and Industrial Microorganisms (NCAIM), Budapest, Hungary, under the below given number-designations:

| | |
|---|---|
| *Micromonospora* sp. IDR-P$_3$ | NCAIM (P) B 001268 |
| *Micromonospora purpurea* IDR-P$_4$ | NCAIM (P) B 001271 |
| *Micromonospora echinospora* ssp. *echinospora* IDR-P$_5$. | NCAIM (P) B 001272 |

-continued

| | |
|---|---|
| *Micromonospora megalomicea* ssp. *nigra* IDR-P$_6$. | NCAIM (P) B 001273 |
| *Micromonospora rosaria* IDR-P$_7$. | NCAIM (P) B 001274 |

Based on the above the invention relates to a new microbial process for the preparation of pravastatin of formula (I)

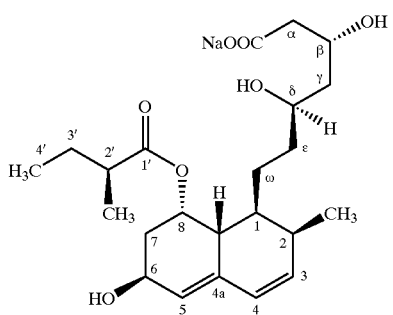

(I)

from a compound of general formula (II),

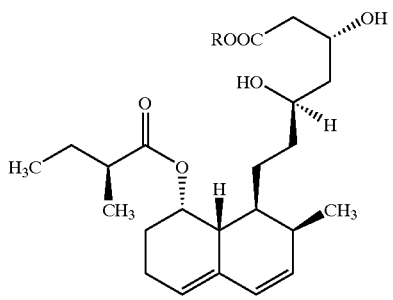

(II)

wherein R stands for an alkali metal or ammonium ion, by the submerged cultivation of a strain which is able to 6β-hydroxylate a compound of formula (II) in aerobic formulation and by the separation and purification of the compound of formula (I) formed in the course of the bioconversion comprising the steps of a) cultivating a strain of a species belonging to the genus *Micromonospora* which is able to 6β-hydroxylate a compound of formula (II)—wherein R is as defined above—on a nutrient medium containing assimilable carbon- and nitrogen sources and mineral salts at 25–32° C., thereafter b) feeding the substrate to be transformed into the developed culture, then c) hydroxylating the substrate until the end of bioconversion, then d) separating the compound of formula (I) from the culture broth and, if desired, purifying the same.

The scope of the invention extends to the wild strains and any mutants of species belonging to the genus *Micromonospora* which are able to hydroxylate the sodium salt of the acid form of compactin to pravastatin.

According to a preferred embodiment of the present invention pravastatin is produced with a *Micromonospora* strain selected from the group consisting of *Micromonospora* sp. IDR-P$_3$ [NCAIM (P) B 001268], *Micromonospora purpurea* IDR-P$_4$ [NCAIM (P) B 001271], *Micromonospora echinospora* IDR-P$_5$ [NCAIM (P) B 001272], *Micromonospora megalomicea* IDR-P$_6$ [NCAIM (P) B 001273] and *Micromonospora rosaria* IDR-P$_7$ [NCAIM (P) B 001274].

According to the most preferred embodiment of the invention pravastatin is produced with *Micromonospora* sp. strain IDR-P$_3$ [NCAIM (P) B 001268].

The present invention can be carried out by in situ fermentation method, that is when, hydroxylation is accomplished with the participation of an actively growing *Micromonospora* culture.

The hydroxylation may be conducted by employing agitation as shake-flask culture or aeration and agitation in fermentors, when the compound of the formula (II) is added to the growing cultures. In such cases an anti-foaming agent may be employed. The adequate density of culture of this strain could be achieved by the use of an appropriate medium containing available carbon and nitrogen sources, inorganic salts as well as trace elements.

E.g. glucose, glycerol, dextrin, starch, rhamnose, xylose, sucrose and soluble starch provided to be assimilable carbon sources while soybean meal, corn steep liquor, peptone, yeast extract, meat extract, ammonium citrate and ammonium sulfate as good nitrogen sources. Inorganic salts such as calcium carbonate, sodium phosphates, potassium phosphates etc., may be added to the culture medium. Preferred media for the growth of this selected strain are those described in the examples.

The bioconversion of compactin to pravastatin can be done by different fermentation techniques, e.g., batch culture, fed-batch culture. Preferably, an agitated liquid submerged culture is used. The preferred temperature is about 25° C. to 37° C., most preferably about 25° C. to 32° C.

The preferred pH is about 6.0 to 9.0, most preferably about 7.0 to 8.5. The preferred shaking condition is about 200 rpm to 400 rpm, most preferably about 250 rpm.

The invention provides a method for converting compactin acid sodium salt to pravastatin. Compactin acid sodium salt can be used in this invention at any concentration which will result in production of pravastatin. Preferably, the compactin concentration is between 0.1 and 10 g/liter, more preferably is between about 0.3 and 3.0 g/liter.

The invention is meant to cover any percentage of conversion of compactin to pravastatin by the strains of *Micromonospora* spp., at least 30% and most preferably at least about 90%.

In the course of the fermentation the composition of the culture broth is controlled by a high performance liquid chromatographic (HPLC) method. According to the HPLC method the sample of the broth is diluted twofold with methanol, centrifuged and the supernatant is used for the analysis. Parameters of the HPLC system used for the analysis are: Waters analytical HPLC equipment; column packing: Waters Novapack C$_{18}$ 5 μm; measurement at 237 nm; injection volume 10 μl; flow rate 0.6–0.9 ml/min linear gradient; gradient elution is used, eluents: solvent A=acetonitrile—0.1M NaH$_2$PO$_4$ in water (25:75), solvent B=acetonitrile-water (pH 2 with H$_3$PO$_4$) (70:30).

Parameters of gradient elution:

| Time (min) | Flow rate (ml/min) | Eluent A (%) | Eluent B (%) |
|---|---|---|---|
| 0 | 0.6 | 100 | 0 |
| 2 | 0.7 | 100 | 0 |
| 12 | 0.9 | 0 | 100 |

-continued

| Time (min) | Flow rate (ml/min) | Eluent A (%) | Eluent B (%) |
|---|---|---|---|
| 21 | 0.9 | 0 | 100 |
| 22 | 0.9 | 100 | 0 |
| 27 | 0.7 | 100 | 0 |

Retention times: pravastatin (Na salt) 10.6 min; compactin (acid Na salt) 19.5 min; pravastatin (lactone form) 17.3 min, compactin (lactone form) 23.5 min.

Any known method can be used for the isolation of pravastatin, e.g., extraction-reextraction, anion exchange chromatography, precipitation.

For the recovery of the product from the broth it is advantageous to take into consideration the fact, that during the bioconversion pravastatin is formed in its acidic form, thus it can be isolated from the filtrate of the broth by its adsorption on an anion exchange resin column. For the isolation of the product it is advantageous to use a strongly basic anion exchange resin which is a polystyrene-divinylbenzene polymer carrying quaternary ammonium active groups e.g. Dowex Al 400 (OH$^-$), Dowex 1×2 (OH$^-$), Dowex 2×4 (OH$^-$), Amberlite IRA 900 (OH$^-$) resins. The product adsorbed on the ion exchange resin can be eluted from the column by aqueous acetic acid or a sodium chloride containing acetone-water mixture, preferably by 1% sodium chloride containing acetone-water (1:1) mixture. Pravastatin containing fractions are combined and the acetone being in the eluate is distilled off in vacuum. The pH of the concentrate is adjusted with 15% sulphuric acid into the range of 3.5–4.0 and the acidified aqueous solution is extracted by ethyl acetate. From the ethyl acetate extract pravastatin can be extracted by 1/10 and 1/20 volume ratio of 5% sodium hydrogen carbonate or weakly alkaline water (pH 7.5–8.0). It was experienced, that pravastatin can be recovered in a pure form from the above obtained alkaline aqueous extract by column chromatography on a non-ionic adsorption resin. An advantageous method is, that first of all the ethyl acetate dissolved in the aqueous phase is removed by vacuum distillation from the alkaline aqueous extract and then the aqueous extract is loaded on a Diaion HP-20 column. Pravastatin adsorbed on the column is purified by elution with aqueous acetone in which the acetone content is gradually increased, then the chromatographic fractions containing pravastatin as a single component are combined and concentrated in vacuum. The concentrate is clarified with charcoal and lyophilized, then crystallized from an ethanol-ethyl acetate mixture, affording pravastatin in a quality acceptable for pharmaceutical application.

After finishing the bioconversion pravastatin can be extracted either from the fermentation broth or from the filtrate obtained after the separation of the micelium mass. The latter can be removed either by filtration or centrifugation, however, it is advantageous especially in an industrial scale to make a whole broth extraction. Before extraction the pH of either the fermentation broth or the filtrate of the broth is adjusted to 3.5–3.7 with a mineral acid preferably with diluted sulphuric acid. The extraction is done with acetic acid ester with a 2–4 carbon atom containing aliphatic alcohol preferably with ethyl acetate or isobutyl acetate. The ethyl acetate extract is washed with water and dried with anhydrous sodium sulphate. Then the lactone derivative is prepared from pravastatin. The lactone ring closure is carried out in dried ethyl acetate solution at room temperature, under continuous stirring by inducing the lactone formation with catalytic amount of trifluoro-acetic acid. The lactone ring closure is checked by thin layer chromatographic analysis (TLC). After finishing the lactone formation the ethyl acetate solution is washed at first with 5% aqueous sodium hydrogen carbonate solution and then with water, and it is dried with anhydrous sodium sulphate and evaporated in vacuum. The residue is purified with silica gel column chromatography used as the eluent mixtures of ethyl acetone-n-hexane with gradually increasing ethyl acetate content. Pravastatin is prepared from the pravastatin lactone by hydrolysis at room temperature in acetone with equivalent quantity of sodium hydroxide. When the pravastatin sodium salt formation has been completed, the pravastatin is precipitated with acetone. Then the precipitate is filtered and washed with acetone and n-hexane and dried in vacuum, then crystallized from an ethanol-ethyl acetate mixture.

It was found, that the chromatography on Sephadex LH-20 gel is advantageously applicable for purifying pravastatin. By application of this method pravastatin exceeding the purity of 99.5% (measured by HPLC) can be produced.

In the course of our experiments the following invention has been recognized: from the organic solvent extract, preferably from the ethyl acetate or isobutyl acetate extract of the broth or the broth filtrate of *Micromonospora* sp. IDR-P$_3$ strain which is able to 6β-hydroxylate a compound of general formula (II), pravastatin can be precipitated as a crystalline salt with secondary amines. Further it was found, that for the salt formation several secondary amines containing alkyl-, cycloalkyl-, aralkyl- or aryl-substituents are appropriate. Expediently non-toxic secondary amines were selected among them, e.g., dioctylamine, dicyclohexylamine, dibenzylamine. The isolation of the organic secondary amine salt intermediates, e.g., the dibenzylamine salt was carried out by adding dibenzylamine in 1.5 equivalent quantity related to the pravastatin content of the extract, then the extract is concentrated by vacuum distillation to 5% of its original volume, then another quantity of dibenzylamine is added into the concentration in 0.2 equivalent ratio. The crystalline dibenzylamine salt is precipitated from the concentrate. The crystalline crude product is filtered and dried in vacuum, and it is clarified with charcoal in methanol or acetone solution. Then with recrystallization of the clarified product from acetone chromatographically pure pravastatin dibenzylamine salt intermediate can be obtained.

Pravastatin organic secondary amine salts can be transformed to pravastatin by sodium hydroxide or a sodium alkoxide preferably sodium ethoxide.

The isolation of pravastatin via a secondary amine salt intermediate is a simpler procedure than any of the ever known isolation procedures. During the procedure artefacts are not formed, and the separation of pravastatin from the by-products of the bioconversion and from the various metabolic products biosynthesized by the hydroxylating microorganism can be advantageously solved.

The process according to the invention is presented by the following examples.

EXAMPLE 1

Spores were obtained from the surface of a 7–10 day old, soluble starch agar (SM) slant culture of *Micromonospora* sp. IDR-P$_3$ [NCAIM (P) B 001268] strain and suspended in 5 ml of sterile distilled water. This suspension was then used to inoculate 100 ml of sterile T1 inoculum medium in a 500 ml Erlenmeyer flask.

| Composition of SM medium | |
|---|---|
| Soluble starch | 10.0 g |
| $Na_2HPO_4$ | 1.15 g |
| $KH_2PO_4$ | 0.25 g |
| KCl | 0.2 g |
| $MgSO_4 \times 7H_2O$ | 0.2 g |
| Agar | 15.0 g |
| in 1000 ml of distilled water | |

The pH of the medium was adjusted to 7.0 before sterilization and the mixture was sterilized at 121° C. for 25 minutes.

| Composition of TI medium | |
|---|---|
| Soluble starch | 20.0 g |
| Yeast extract | 10.0 g |
| in 1000 ml of tap water | |

The pH was adjusted to 7.0 before sterilization and heat treated at 121° C. for 25 minutes.

The developing culture was shaken on a rotary shaker (250 r.p.m.; and amplitude: 2.5 cm) for 3 days, at 32° C., then 5 ml aliquots from it were used to inoculate 10 Erlenmeyer flasks of 500 ml volume each containing 100 ml of TT medium sterilized at 121° C. for 25 minutes.

| Composition of TT medium | |
|---|---|
| Potato starch | 30.0 g |
| Soybean meal | 30.0 g |
| $CaCO_3$ | 5.0 g |
| $CoCl_2 \times 6H_2O$ | 2.0 mg |
| Palm oil | 2.0 g |
| in 1000 ml of tap water | |

The pH was adjusted to 7.0 before heat sterilization.

The incubation was carried out at 32° C. for 72 hours then 50 mg of compactin acid sodium salt was added to each flask in distilled water, and the cultivation was carried out for 96 hours. The conversion rate of compactin acid sodium salt into pravastatin measured by HPLC was 82%.

After finishing the fermentation the cultures were united, and from the obtained collective fermentation broth, which contained 410 mg of pravastatin, the isolation of the latter was carried out as follows: The fermentation broth was centrifuged at 2500 r.p.m. for 20 min. The supernatant of the broth and the mycelial mass were separated, then the latter was resuspended in 250 ml of water and the obtained suspension was stirred for one hour and filtered. The pH of the combined centrifuged broth and the filtrate was adjusted by 15% sulphuric acid to 4.0, then the acidic filtrate was extracted with 3×300 ml of ethyl acetate. The combined ethyl acetate extracts were washed with 300 ml of water, dried with anhydrous sodium sulphate and concentrated in vacuum to 100 ml volume. Then pravastatin lactone was prepared from pravastatin by adding trifluoroacetic acid in catalytical amount at room temperature under continuous stirring. Formation of pravastatin lactone was controlled by TLC method: adsorbent: Kieselgel 60 $F_{254}$ DC (Merck) aluminium foil; developing solvent acetone-benzene-acetic acid (50:50:1.5) mixture; detection: with phospho-molybdic acid reagent. The $R_f$ value of pravastatin lactone was 0.7.

After the completion of the lactone formation the ethyl acetate was washed with 2×20 ml of 5% aqueous sodium hydrogen carbonate then washed with 20 ml of water, dried with anhydrous sodium sulphate and evaporated in vacuum, 0.5 g of evaporation residue was obtained, which was chromatographed on 10 g of Kieselgel 60 adsorbent containing column (diameter of the column: 1.2 cm. height of the adsorbent bed: 17 cm). For elution ethyl acetate-n-hexane mixtures were used in which the ethyl acetate content was gradually increased. Pravastatin lactone was eluted from the column with the mixture of 60% ethyl acetate-40% n-hexane. The fractions containing pravastatin lactone were combined and evaporated in vacuum. The residue obtained, which contained 230 mg of pravastatin lactone, was dissolved in 5 ml of acetone and then under stirring 110 mole % of sodium hydroxide was added in 1M ethanolic solution. Stirring of the solution was continued for half an hour at room temperature. Subsequently, the solution was concentrated to 2 ml volume and 4 ml of acetone was added to the concentrate. The mixture was kept at +5° C. overnight. The precipitate was filtered, washed with 2 ml of acetone and then with 2 ml of n-hexane and dried in vacuum at room temperature. The resulting crude pravastatin was dissolved in ethanol, clarified by charcoal, then crystallized from ethanol-ethyl acetate mixture. In this way 170 mg of pravastatin was obtained.

Melting point 170–173° C. (decomp.) $[\alpha]_D^2 = +156°$ (c=0.5, in water). Ultraviolet absorption spectrum (20 μg/ml, in methanol): $\lambda_{max}$=231, 237, 245 nm (log ε=4.263; 4.311; 4.136). Infrared absorption spectrum (KBr): νOH 3415, νCH 2965, νC=O 1730, νCOO⁻ 1575 cm⁻¹. ¹H-NMR spectrum ($D_2O$, δ, ppm): 0.86, d, 3H (2-$CH_3$); 5.92, dd, J=10.0 and 5.4 Hz, 1H (3-H); 5.99, d, J=10.0 Hz, 1H (4-H); 5.51, br, 1H (5-H); 4.24, m, 1H (6-H); 5.34, br, 1H (8-H); 4.06, m, 1H (β-H), 3.65, m, 1H (δ-H); 1.05, d, 3H (2'-$CH_3$); 0.82, t, 3H (4'-$H_3$).

¹³C-NMR spectrum ($D_2O$, δ, ppm): 15.3, q (2-$CH_3$); 139.5, d (C-3); 129.5, d (C-4); 138.1, s (C-4a); 127.7, d (C-5); 66.6, d (C-6); 70.1, d (C-8); 182.6, s (COO–); 72.6, d (C-β); 73.0, d (C-δ); 182.0, s (C-1'); 18.8, q (2'-$CH_3$); 13.7, q (C-4').

Positive FAB mass spectrum (characteristic ions): [M+Na]⁺ 469; [M+H]⁺ 447. Negative FAB mass spectrum (characteristic ions): [M–H]⁻ 445, [M–Na]⁻ 423, m/z 101 [2-methyl-butyric acid-H]⁻.

EXAMPLE 2

10 Erlenmeyer flasks of 500 ml volume each containing 100 ml of MT, bioconversion medium were inoculated with inoculum culture prepared as described in Example 1, then incubated at 28° C. for 96 hours and 50 mg of compactin acid sodium salt was added to each flask in distilled water, then the hydroxylation was carried out for 72 hours when another 50—50 mg of substrate was added to the cultures in distilled water and the fermentation was continued for 72 hours.

| Composition of $MT_1$ bioconversion medium | |
|---|---|
| Potato starch | 10.0 g |
| Dextrose | 20.0 g |
| Soybean meal | 10.0 g |
| Yeast extract | 10.0 g |
| $CaCO_3$ | 5.0 g |
| Sunflower oil | 2.0 g |
| in 1000 ml of tap water | |

The pH of the bioconversion medium was adjusted to 7.0 before sterilization. The mixture was sterilized at 121° C. for 25 minutes.

After finishing the bioconversion period the cultures were united and the pravastatin was isolated from the collective broth according to the following procedure:

The united broth, which contained 750 mg of pravastatin according to the HPLC assay was centrifuged at 2500 r.p.m. for 20 min. The separated micelium mass was stirred with 250 ml of water for an hour, then filtered. The centrifuged broth and the filtrate were combined and the pH of the resulting solution was adjusted to a 3.5–4.0 value, with 15% sulphuric acid, then the solution was extracted with 3×300 ml of ethyl acetate. Then 150 mole % of dibenzylamine—calculated for the pravastatin content—was added to the ethyl acetate extract. The ethyl acetate extract was evaporated to about 30 ml volume and the suspension was kept overnight at 0–5° C. The precipitated pravastatin acid dibenzylamine salt was filtered and washed on the filter with cooled ethyl acetate and n-hexane, finally dried in vacuum. The 1.1 g of crude pravastatin acid dibenzylamine salt was dissolved in 33 ml of acetone at 62–66° C. temperature, and the solution was clarified with 0.1 g of charcoal for half an hour. Then the charcoal was removed by filtration from the solution. Crystals precipitated from the clarified solution were dissolved again at the above temperature, then the solution was kept at +5° C. overnight. The precipitate was filtered, washed with cooled acetone and n-hexane and dried in vacuum. Pravastatin acid dibenzylamine salt obtained (0.7 g) was suspended in 10 ml of ethanol, then 110 mole % of sodium hydroxide was added to the solution by feeding 1M aqueous solution. Stirring of the alkaline solution was continued for half an hour at room temperature. After the completion of the sodium salt formation 30 ml of water was added and the pH of the solution was neutralized, then ethanol was distilled off in vacuum. The aqueous concentration was chromatographed on a column filled with 50 ml of Diaion HP 20 resin (diameter of the column: 1.5 cm, height of the resin bed: 28 cm). The column was eluted with acetone-deionized water mixtures, where the concentration of the acetone was increased in 5% steps. Pravastatin could be eluted from the column by a 15% acetone containing acetone-deionized water mixture. Fractions were analysed by TLC method given in the Example 1. The $R_f$ value of pravastatin was 0.5. Fractions containing pravastatin were combined and the acetone content was evaporated in vacuum. By the lyophilization of the aqueous residue 390 mg of chromatographically pure pravastatin was obtained.

EXAMPLE 3

4.5 liters of TT/2 medium, in a laboratory fermentor, were sterilized at 121° C. for 45 minutes and inoculated with 500 ml of inoculum shake culture prepared as described in Example 1, then incubated at 32° C., aerated with 250 l of sterile air/h and stirred with a flat blade stirrer at 300 r.p.m. The incubation was continued for 72 hours and 2.5 g of compactin acid sodium salt was added to the culture. After $48^{th}$ hour of the bioconversion period the compactin substrate was completely consumed from the fermentation broth, then an additional 2.5 g of compactin acid sodium salt was added again into the culture. The second dose of compactin was consumed within 24 hours. The conversion rate of compactin acid sodium salt into pravastatin was about 90% in the bioconversion process.

| Composition of TT/2 bioconversion medium | |
|---|---|
| Glucose | 75.0 g |
| Soluble starch | 50.0 g |
| Soybean meal | 50.0 g |
| Yeast extract | 50.0 g |
| Pepton | 5.0 g |
| NaNO$_3$ | 20.0 g |
| CaCO$_3$ | 25.0 g |
| in 4500 ml of tap water | |

EXAMPLE 4

4.5 liters of the TT/1 fermentation medium, in a laboratory fermentor were sterilized at 121° C. for 45 minutes and inoculated with 500 ml of the inoculum shake culture prepared as described in Example 1, then incubated at 28° C. aerated with 200 l sterile air/h and stirred with a flat blade stirrer at 400 r.p.m.

| Composition of TT/1 bioconversion medium | |
|---|---|
| Glucose | 125.0 g |
| Potato starch | 25.0 g |
| Soybean meal | 50.0 g |
| Yeast extract (Gistex) | 50.0 g |
| Pepton | 50.0 g |
| CoCl$_2$x6H$_2$O | 10.0 mg |
| Sunflower oil | 10.0 g |
| in 4500 ml of tap water | |

The pH of the bioconversion medium was adjusted to 7.0 before sterilization.

Cultivation was continued at 28° C. for 96 hours. At this time 2.5 g of compactin acid sodium salt was added in sterile filtered aqueous solution to the culture. By the $5^{th}$ day of fermentation the compactin acid sodium salt was completely consumed from the fermentation broth. Then the substrate feeding was repeated daily for further 3 days in 2.5 g/day portions. The compactin acid sodium salt substrate was gradually consumed during the four days and converted completely to pravastatin. According to the results of HPLC measurements at the end of the fermentation period from 10 g of compactin substrate 9 g of pravastatin has been produced.

After finishing the bioconversion the pravastatin formed in the concentration of 1800 µg/ml was isolated as follows:

5 liters of culture broth were centrifuged at 2500 r.p.m. for 20 min. Then 2 liters of water were added to the separated mycelial mass and the suspension was stirred for one hour and filtered. These two filtrates were united and passed through with a flow rate of 500 ml/hour on a column containing 300 g (540 ml) of Dowex Al 400 (OH$^-$) resin (diameter of the column: 4 cm, height of the resin bed: 43 cm), then the resin bed was washed with 1 liter of deionized water. Thereafter the column was eluted with 1 liter of acetone-water (1:1) mixture containing 10 g of sodium chloride by collecting 50 ml fractions. The fractions were analysed by the TLC method given in the Example 1. Fractions containing the product were combined and the acetone was distilled off in vacuum. The pH of the concentrate was adjusted to 3.5–4.0 value by 15% sulphuric acid, then it was extracted 3×250 ml of ethyl acetate. 40 ml of deionized water was added to the combined ethyl acetate extract, then the pH was adjusted to 7.5–8.0 value by 1M sodium hydroxide. After 15 min stirring the aqueous and ethyl acetate phases were separated, then the ethyl acetate solution was extracted with 2×40 ml of deionized water as it was written before. Then the combined alkaline aqueous solution was concentrated to 50 ml volume and chromatographed on a column filled with 600 ml of Diaion HP20 (Mitsubishi Co., Japan) non ionic adsorbent resin (diameter of the column: 3.8 cm, height of the resin bed: 53 cm). The column was washed with 600 ml of deionized water, then eluted with acetone-deionized water mixtures, where the concentration of acetone was increased in 5% steps, collecting 50 ml fractions. The eluate was analysed by TLC method given in the Example 1. Pravastatin was eluted from the column by an acetone-deionized water mixture containing 15% of aceton. Fractions containing pravastatin as single component were combined and the solution was concentrated in vacuum to 150 ml volume. Subsequently, 0.6 g of charcoal was added to the concentrated aqueous solution and pravastatin was clarified at room temperature for 1 hour. Then the charcoal was filtered and the filtrate was lyophilised. The resulting 6.5 g of lyophilised pravastatin was crystallized twice from a mixture of ethanol and ethyl acetate. The precipitate was filtered and washed with 20 ml of ethyl acetate and 20 ml of n-hexane, and dried in vacuum at room temperature. Thus 4.6 g of chromatographically pure pravastatin was obtained.

EXAMPLE 5

A spore suspension was prepared with 5 ml of sterile distilled water from the surface of a 10 days old, soluble starch agar slant culture, as described in Example 1, of *Micromonospora echinospora* ssp. *echinospora* IDR-P$_5$ [NCAIM (P) B 001272] strain—being able for the 6β-hydroxylation of compactin acid sodium salt—and the obtained spore suspension was used to inoculate 100 ml of inoculum medium T1 sterilized in a 500 ml Erlenmeyer flask. Composition of the medium T1 was also described in Example 1. The inoculated medium was shaken on a rotary shaker (250 r.p.m., 2.5 cm amplitude, for 3 days at 28° C., then 5 ml aliquots of the developed culture were transferred into 100—100 ml of bioconversion medium TT/1 sterilized in 500 ml Erlenmeyer flasks for 25 min at 121° C. Composition of the medium TT/1 is described in Example 4. Flasks were shaken on a rotary shaker (250 r.p.m., 2.5 cm amplitude) for 3 days at 25° C., then 10—10 mg of compactin substrate (compactin acid sodium salt) was added in sterile filtered aqueous solution into the cultures, then the fermentation was continued for 168 hours.

At the end of the bioconversion the pravastatin content of the fermentation broth was determined by an HPLC method. At this time the average pravastatin concentration was 40 µg/ml.

EXAMPLE 6

The fermentation, substrate feeding and bioconversion were carried out with strain IDR-P$_6$, [NCAIM (P) B 001273] of *Micromonospora megalomicea* ssp. *nigra* as it was written in Example 5. The pravastatin content of the fermentation broth was determined by an HPLC method. At the end of the bioconversion the pravastatin content of the broth was 50 µg/ml.

EXAMPLE 7

5 ml aliquots of an inoculum culture of strain IDR-P$_4$ [NCAIM (P) B 001271] of *Micromonospora purpurea* prepared as described in Example 1 were used to seed 100— 100 ml of TT/14 medium dispensed in 500 ml Erlenmeyer flasks and sterilized for 25 min at 121° C.

| Composition of medium TT/14 | |
|---|---|
| Potato starch | 5.0 g |
| Glucose | 25.0 g |
| Yeast extract (GISTEX) | 15.0 g |
| Pepton | 15.0 g |
| CaCO$_3$ | 1.0 g |
| in 1000 ml of tap water | |

The pH of the bioconversion medium was adjusted to 7.0 before sterilization.

Flasks were shaken on a rotary shaker (250 r.p.m., 2.5 cm amplitude) for 3 days. The substrate feeding, the bioconversion and determination of the pravastatin content were carried out as described in Example 5. At the end of the bioconversion the pravastatin content of the fermentation broth was 40 µg/ml.

EXAMPLE 8

The fermentation, substrate feeding and bioconversion were carried out with strain IDR-P$_7$, [NCAIM (P) B 001274] of *Micromonospora rosaria* as it was written in Example 1. At the end of the bioconversion 350 µg/ml pravastatin was measured in the fermentation broth by HPLC method.

What we claim is:
1. A microbial process for the preparation of the compound of formula (I)

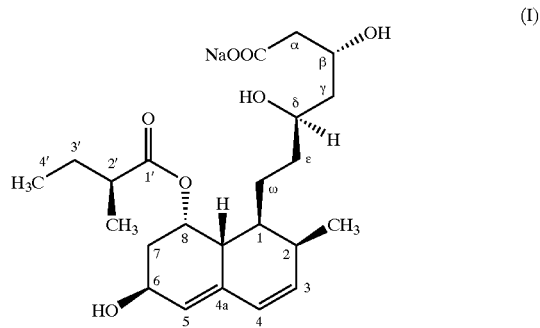

from a compound of the general formula (II)

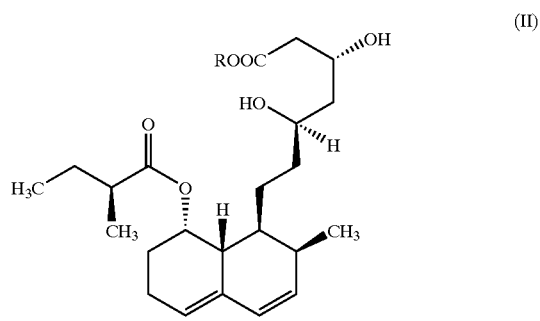

wherein R stands for an alkali metal or ammonium ion, by the submerged culture of a *Micromonospora* strain which is able to 6β-hydroxylate a compound of formula (II) under aerobic conditions and by the separation and purification of the compound of formula (I) formed in the course of the bioconversion comprising the steps of a) cultivating a *Micromonospora* strain which is able to 6β-hydroxylate a compound of formula (II)—wherein R is as defined above—at 25–32° C. on a nutrient medium containing available carbon- and nitrogen sources and mineral salts, thereafter b) feeding the substrate to be transformed into a developing culture, then c) hydroxylating the substrate until finishing of the bioconversion, then d) separating the compound of formula (I) from the culture broth and, if desired, purifying the same.

2. A process as claimed in claim 1, wherein the *Micromonospora* sp. IDR-$P_3$ strain deposited at the National Collection of Agricultural and Industrial Microorganisms, Budapest, Hungary under the number NCAIM (P) B 001268 or a mutant strain thereof which is able to 6β-hydroxylate a compound of general formula (II) is applied.

3. A process as claimed in claim 1, wherein the *Micromonospora purpurea* IDR-$P_4$ strain deposited at the National Collection of Agricultural and Industrial Microorganisms, Budapest, Hungary under the number NCAIM (P) B 001271 or a mutant strain thereof which is able to 6β-hydroxylate a compound of general formula (II) is applied.

4. A process as claimed in claim 1, wherein the *Micromonospora echinospora* ssp. *echinospora* IDR-$P_5$ strain deposited at the National Collection of Agricultural and Industrial Microorganisms, Budapest, Hungary under the number NCAIM (P) B 001272 or a mutant strain thereof which is able to 6β-hydroxylate a compound of general formula (II) is applied.

5. A process as claimed in claim 1, wherein the *Micromonospora megalomicea* ssp. *nigra* IDR-$P_6$ strain deposited at the National Collection of Agricultural and Industrial Microorganisms, Budapest, Hungary under the number NCAIM (P) B 001273 or a mutant strain thereof which is able to 6β-hydroxylate a compound of general formula (II) is applied.

6. A process as claimed in claim 1, wherein the *Micromonospora rosaria* IDR-$P_7$ strain deposited at the National Collection of Agricultural and Industrial Microorganisms, Budapest, Hungary under the number NCAIM (P) B 001274 or a mutant strain thereof which is able to 6β-hydroxylate a compound of general formula (II) is applied.

7. A process as claimed in anyone of claim 1 to 6, wherein the compound of formula (I) formed during the fermentation is separated from the culture broth by adsorption on an anionic ion exchange resin or by extraction with a water immiscible organic solvent, followed by the preparation of its lactone derivative or its secondary amine salt as an intermediate, or by purification of the alkaline aqueous extract obtained from the organic solvent extract of the fermentation broth with chromatography on a non-ionic adsorbing resin.

* * * * *